United States Patent [19]

Dysarz

[11] Patent Number: 4,973,316

[45] Date of Patent: Nov. 27, 1990

[54] ONE HANDED RETRACTABLE SAFETY SYRINGE

[76] Inventor: Edward D. Dysarz, 11423 Triola Lane, Houston, Tex. 77072

[21] Appl. No.: 466,722

[22] Filed: Jan. 16, 1990

[51] Int. Cl.⁵ .............................................. A61M 5/32
[52] U.S. Cl. .................................... 604/195; 604/198; 604/110
[58] Field of Search ............... 604/187, 195, 198, 263, 604/110

[56] References Cited

U.S. PATENT DOCUMENTS

| | | | |
|---|---|---|---|
| 4,747,831 | 5/1988 | Kulli | 604/198 X |
| 4,838,863 | 6/1989 | Allard et al. | 604/195 X |
| 4,850,977 | 7/1989 | Bayless | 604/198 |
| 4,874,382 | 10/1989 | Lindemann et al. | 604/195 |

Primary Examiner—John D. Yasko

[57] ABSTRACT

A disposable hypodermic syringe having a needle fixed to a piston assembly. The piston assembly is held within the barrel of said hypodermic syringe by a compressed spring and a trigger. When said trigger is disengaged with said piston assembly said spring pushed said piston assembly and said needle into said barrel of said hypodermic syringe and holds said needle fixed to said piston assembly within said barrel thus preventing any accidental injection of bacteria, virus or other undesirable material into others. The disengagement of said trigger with said piston assembly is accomplished with only one and the same hand that is used to inject the needle of the syringe into a body.

16 Claims, 6 Drawing Sheets

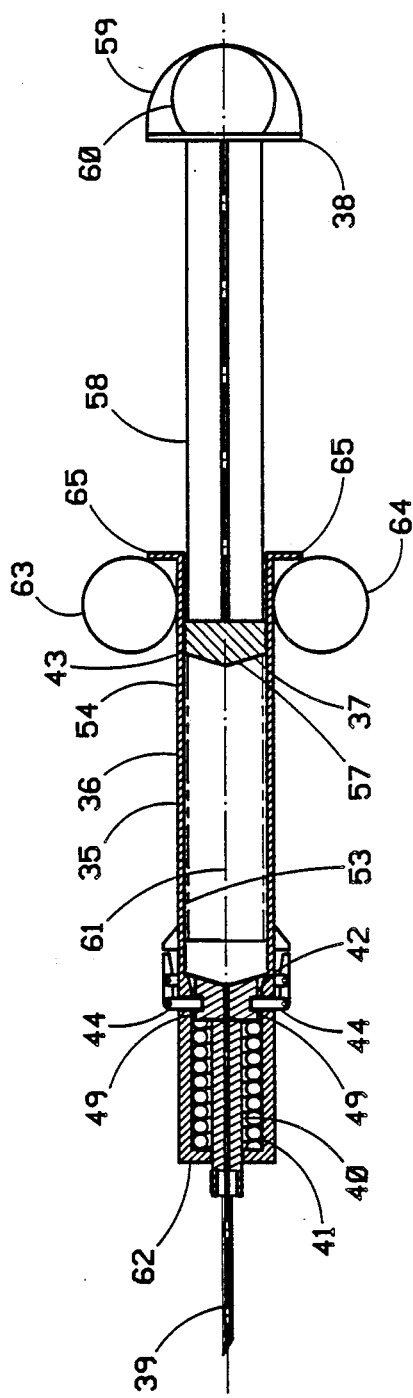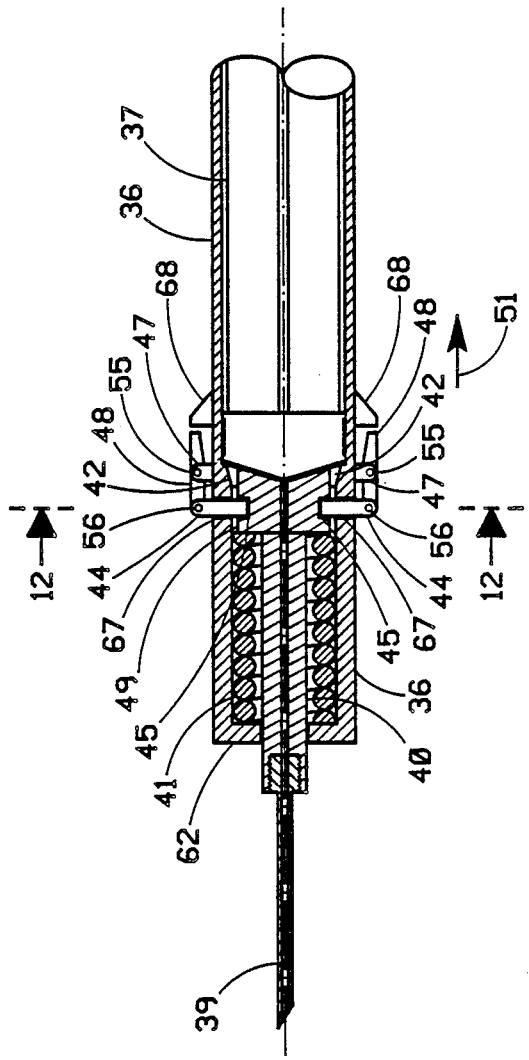
FIGURE 8
FIGURE 9

ONE HANDED RETRACTABLE SAFETY SYRINGE

BACKGROUND OF THE INVENTION

There are many safety syringe designs available today. Some of these designs have a sleeve or a sheath that will cover the needle after it has been used. Some typical designs with sleeves or sheaths are Z. M. ROEHR et al U.S. Pat. No. 3,008,570, Z. M. ROEHR U.S. Pat. No. 3,107,785, BARTNER, et al U.S. Pat. No. 3,895,633, G. K. BURKE U.S. Pat. No. 3,306,291, GYURE et al U.S. Pat. No. 4,300,678, WINSTEAD HALL U.S. Pat. No. 4,356,822, SAMPSON U.S. Pat. No. 4,425,120, LARSON U.S. Pat. No. 4,639,249, HARBAUGH U.S. Pat. No. 4,655,751, STRAUSS U.S. Pat. No. 4,664,654, BRAGINETZ U.S. Pat. No. 4,666,435, SPENCER U.S. Pat. No. 4,702,738, MILORAD U.S. Pat. No. 4,702,739, SPENCER U.S. Pat. No. 4,801,295, PONCY U.S. Pat. No. 4,816,022, and HUGHES U.S. Pat. No. 4,840,619.

Other designs have a retractable needle such as WELTMAN U.S. Pat. No. 3,306,290, and DENT U.S. Pat. No. 4,392,859. These designs do not have a means whereby the needle is extended from the syringe and held in place in a positive and rigid position in order to first inject the needle prior to injecting the medication. Still other designs have methods of bending the needle to render it harmless after the medication has been injected. Most of these designs have one major purpose and that is to prevent the spread of infectious diseases such as aids, hepatitis or other diseases from an accidental injection with a contaminated needle, into others after the needle of the syringe was inserted into a patient with the above mentioned disease. These various designs all work well up to a degree, but they all fall short of their intended purpose during the act of covering the needle, or removing the needle.

All of these designs require at lease two hands to operate. The use of two hands to cover the contaminated needle is most unsatisfactory in that during the act of placing a second hand on the syringe the person holding the syringe in one hand may be bumped and accidently inject the needle into their other hand before it can grasp the syringe. Other accidental jabbings or injections can happen in an ambulance where just as a person tries to grasp the contaminated syringe, the ambulance can hit a bump in the road causing the person holding the syringe to accidentally stick another person or themselves with the contaminated needle. The need has developed for a syringe that will cover the contaminated needle with the use of only one hand.

SUMMARY

It is the object of this invention to provide a syringe wherein the needle of the syringe is retracted into the barrel of the syringe and protected from an accidental pricking after it has been used; the needle can be retracted into the barrel with the use of only one hand and that one hand being the hand that was used to inject the needle into a patient.

Another object of the present invention is to render the syringe useless after the needle is retracted into the barrel of the syringe and to prevent the accidental reuse of the contaminated syringe or to further prevent the reuse and abuse by users of illicit drugs.

It is still another object of the present invention to allow for the safe disassembly of the contaminated syringe for better and safer disposal means.

The foregoing and other objects and advantages are attained by a hypodermic syringe, syringe barrel, needle, spring, piston assembly and plunger assembly in combination with a trigger means wherein when said syringe is used to inject a drug or other material into a patient, the trigger is released and the spring further pushes the needle fixed to the piston assembly into the barrel of the syringe rendering the contaminated needle of the syringe harmless to prevent the accidental pricking of others.

In accordance with another feature of the invention the seal or gasket on the piston assembly will be made out of a material that will tear when the piston assembly moves into the barrel of the syringe, thus rendering the syringe useless for further use for illegal or unauthorized purposes.

In accordance with still another feature of the present invention, the syringe can be safely dissembled and the needle with the piston assembly can be safely dumped into a container for further destruction.

The features of the present invention can be best understood together with further objects and advantages by reference to the following descriptions taken in connection with the accompanying drawings, wherein like numerals indicate like parts.

BRIEF DESCRIPTION OF THE DRAWINGS

FIG. 8 is a section elevation view of a second preferred embodiment of the present invention.

FIG. 9 is an enlarged section elevation view of a second preferred embodiment showing the plunger assembly compressing the spring and held in place by trigger.

DETAILED DESCRIPTION OF THE PREFERRED EMBODIMENTS

Figure 1:
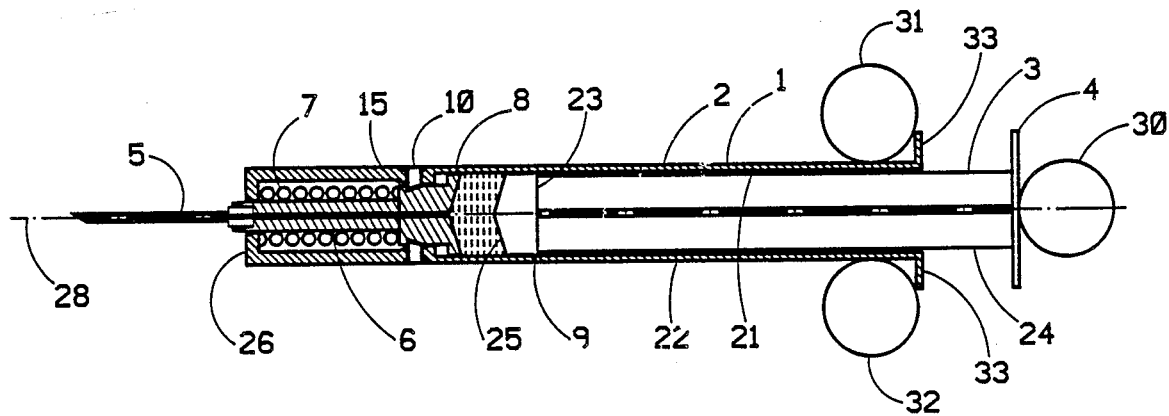
FIG. 1 is a section elevation view of a first preferred embodiment of the present invention

Referring to FIG. 1 there is shown a section elevation view of the the syringe assembly 1 of the first preferred embodiment.

The syringe assembly 1 is comprised of an elongated hollow barrel 2 which is a round tube like in configuration with a first end and a second end and with an inner surface 21 and an outer surface 22. Inside of the elongated hollow barrel 2 is the slideable plunger assembly 3. The slideable plunger assembly 3 with a first end and a second end has a thumb flat 4 at the second end and a plunger piston 23 at the first end. The thumb flat 4 is fixed to the plunger piston 23 by the plunger rod 24. The plunger piston 23 also has a plunger gasket 9 which forms a liquid tight and gas tight seal between the plunger piston 23 and the inner surface 21 of the elongated hollow barrel 2.

The elongated hollow barrel has a longitudinal axis 28 in the center of the elongated hollow barrel. The longitudinal axis 28 has a first end and a second end and runs the entire length of the elongated hollow barrel from the thumb flat 4 to the needle cannula 5.

Also shown inside of the elongated hollow barrel 2 is the slideable piston assembly 6. The slideable piston assembly 6 has a first end and a second end and is comprised of the piston 25, the needle cannula 5 fixed to the first end of the slideable piston assembly 6 and a piston gasket 8 fixed at the second end of the slideable piston assembly 6.

The slideable piston assembly 6 is shown held in place by the barrel flange 26 near the first end of the slideable piston assembly 6 and the piston gasket 8 at the second end of the slideable piston assembly 6. The slideable piston assembly 6 is further held in place by a partly compressed spring 7. The partly compressed spring 7 has a first end resting on the barrel flange 26 and a second end resting on the piston flange 15. The partly compressed spring 7 is pushing on the piston flange 15 of the slideable piston assembly 6. The slideable piston assembly 6 is held and fixed in place by the slideable trigger 10 on each side of the elongated hollow barrel 2.

The syringe assembly 1 is shown held between finger 31 and finger 32 and it is further held and restrained from moving between finger 31 and finger 32 by finger stops 33. The slideable plunger assembly 3 is depressed or pushed by pressure from the thumb 30 on the thumb flat 4.

Figure 2:
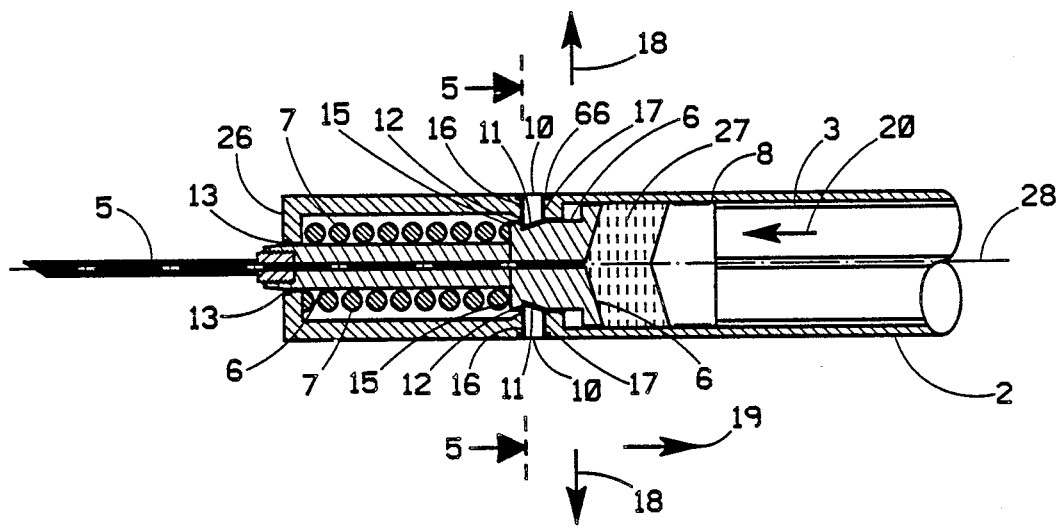
FIG. 2 is an enlarged section elevation view of the first preferred embodiment as taken from FIG 1.

Referring to FIG. 2 there is shown an enlarge partial section elevation of FIG. 1.

The slideable plunger assembly 3 is shown moving in a needleward direction 20 forcing medicament 27 through the cannula 29 in the slideable piston assembly 6 and further through the needle cannula 5 and into a body not shown or part of a body not shown. The needle cannula 5 is shown with a first end and second end, the first end has a point that will enter a body and the second end is shown fixed to the slideable piston assembly 6.

As noted in FIG. 1, the spring 6 is shown only partly compressed, with the first end of the spring resting on the barrel flange 26 and the second end of the spring 6 pushing on the piston flange 15. The slideable piston assembly 6 and needle cannula 5 are held firmly and rigidly in the elongated hollow barrel 2 by the combination of the barrel flange 26 supporting the first end of the slideable piston assembly 6 and the piston gasket 8 at the second end of the slideable piston assembly 6; this prevents movement of the slideable piston assembly 3 and the needle cannula 5 in a direction perpendicular to the longitudinal axis 28 of the elongated hollow barrel 2. The slideable piston assembly 6 and the needle cannula 5 are also held firmly and rigidly within the elongated hollow barrel 2 by the spring 7 that is partly compressed and is thrusting against the barrel flange 26 and the piston flange 15 in combination with the one or two slideable triggers 10 that restrain the spring 7 from thrusting the slideable piston assembly 6 and needle 5 in a thumbward direction 19.

The slideable trigger 10 has a first end and a second end and is held in place at the first end and supported within the elongated hollow barrel 2 by a left guide 16 and a right guide 17. The slideable trigger 10 extends from the left guide 16 and the right guide 17 of the elongated hollow barrel 2 into the trigger notch 12 that is cut into the slideable piston flange 15 of the piston assembly 6.

The slideable trigger 10 is further shown with a trigger slope 11 that slopes in an outward direction 18 and a thumbward direction 19. The trigger notch 12 has a cut that is perpendicular to the longitudinal axis 28 of the elongated hollow barrel 2 and it also has a trigger notch slope 14 that is parallel to the trigger slope 11 on the second end of the slideable trigger 10. The slideable trigger 10 is held in place within the elongated hollow barrel 2 and the trigger notch 12 by friction or other suitable means.

Also shown in FIG. 2 is the barrel flange gasket 13 that will also assist in the support of the slideable piston assembly 6 and will further prevent the area around the spring 7 from being contaminated. The needle cannula 5 is shown threaded into the slideable piston assembly 6 but this is a matter of design choice. A trigger gasket 66 may also be placed over or around the area where the trigger 10 penetrates the elongated hollow barrel 2 to prevent contamination but this is a matter of design choice.

Figure 3:
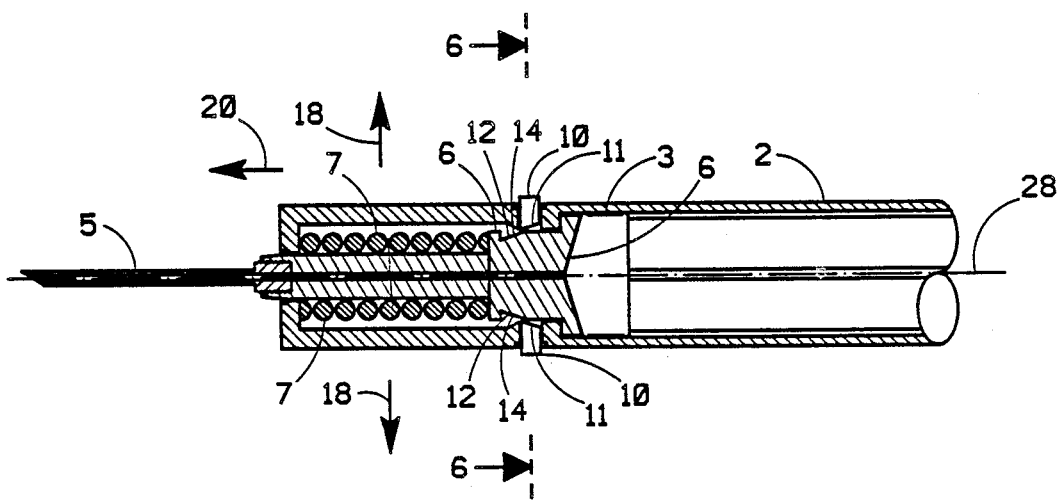
FIG. 3 is an enlarged section elevation view of the first preferred embodiment showing the plunger assembly pushing the piston assembly and compressing the spring.

Referring to FIG. 3 there is shown a partial section elevation of the first preferred embodiment of the present invention. The medicament has already been discharged and the needle cannula 5 has been withdrawn from the body not shown or part of the body not shown.

The slideable plunger assembly 3 is pushed further in a needleward direction 20 by pressure from the thumb not shown in FIG. 3, on the slideable plunger assembly 3 further pushing the slideable piston assembly 6 and needle cannula 5 in a needleward direction 20, further compressing the spring 7. As the slideable piston assembly 6 is moved in a needleward direction 20, the trigger notch slope 14 of the trigger notch 12 reacts with the trigger slope 11 of the sliding trigger 10 thus forcing the sliding trigger 10 to move in an outward direction 18 that is a direction perpendicular to the longitudinal axis 28 of the elongated hollow barrel 2.

As the slideable trigger 10 is moved in an outward direction 18, it will either fall out or be held in place within the barrel by function, which is a matter of design choice.

Figure 4:
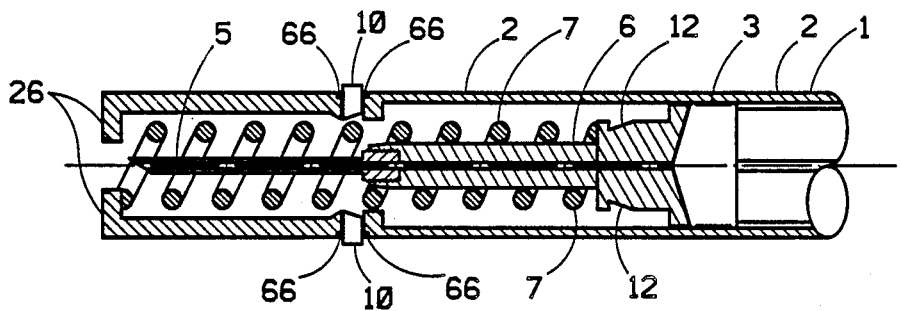
FIG. 4 is an enlarged section elevation view of the first preferred embodiment showing the piston assembly with the needle pushed into the barrel of the syringe by the spring.

Referring to FIG. 4, there is shown a partial section elevation of the first preferred embodiment of the present invention. The slideable trigger 10 has been moved out of the trigger notch 12 and the thumb shown in FIG. 1 is removed from the thumb flat thus allowing the spring 7 to push the slideable piston assembly 6 and the needle cannula 5 into the elongated hollow barrel 2, where the needle cannula 5 will be completely covered by the elongated hollow barrel 2 and the barrel flange 26. The spring 7 may have sufficient force to push the sliding plunger assembly 3 partly out of the hollow elongated barrel 2 of the syringe assembly I.

With the spring 7 constantly pushing or thrusting the slideable piston assembly 6 into the hollow elongated barrel 2, the needle cannula 5 fixed to the slideable piston assembly 6 cannot fall to a position where the point of the needle cannula 5 is exposed outside of the confines of the hollow elongated barrel 2 and the barrel flange 26.

Figure 5:
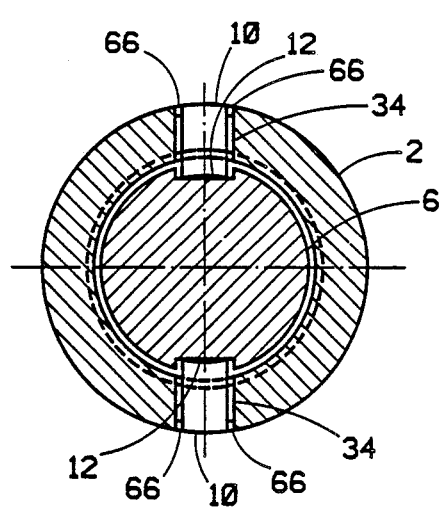
FIG. 5 is an enlarged section elevation as taken through FIG. 2.

Referring to FIG. 5, there is shown a section elevation view of the first preferred embodiment as taken through FIG. 2. The slideable trigger 10 is shown in the trigger notch 12 of the slideable piston assembly 6. The slideable trigger 10 is also shown in the trigger slot 34 of the barrel 2.

Figure 6:
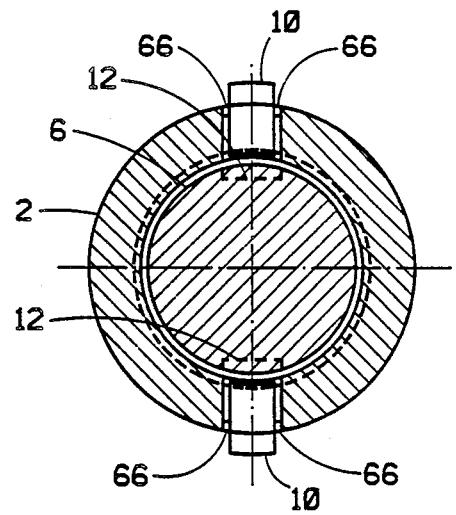
FIG. 6 is an enlarged section elevation as taken through FIG. 3.

Referring to FIG. 6 there is shown a section elevation view of the first preferred embodiment as taken through FIG. 3. The slideable trigger 10 is shown pushed out from the trigger notch 12 of the slideable piston assembly 6. The slideable trigger 10 is also shown projecting out of the elongated hollow barrel 2 of the syringe assembly 1.

Figure 7:
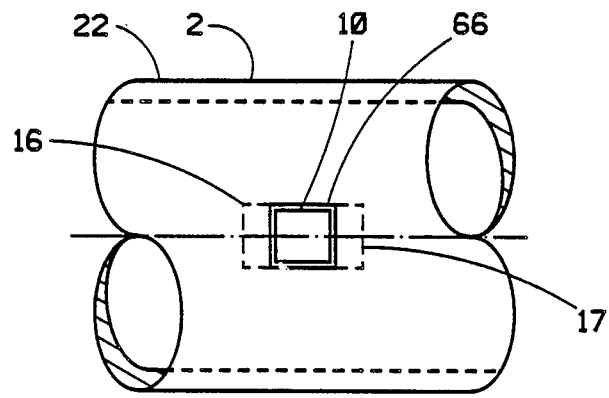
FIG. 7 is a partial plan view as taken from FIG. 2.

Referring to FIG. 7, there is shown a partial elevation of the outer surface 22 of the hollow elongated barrel 2. The slideable trigger 10 is shown as being square however it could also be round or rectangular by design choice. The left guide 16 and the right guide 17 are shown with hidden lines Referring to FIG. 8, there is shown a section elevation view of the syringe assembly 35 of the second preferred embodiment.

The syringe assembly 35 is comprised of a elonged hollow barrel 36 which is a round tube in section with an inner surface 53 and an outer surface 54. Inside of the elonged hollow barrel 36 is the slideble plunger assembly 37. The slideable plunger assembly 37 has a thumb flat 38 at the first end and a plunger piston 57 at the second end. The thumb flat 38 is fixed to the plunger piston 57 by a plunger rod 58. The thumb flat 38 has a thumb ring 59 that holds the thumb 60 of the user of the syringe assembly 35 to the thumb flat 38. The slideable plunger piston 57 also has at least one plunger gasket 43 that forms a liquid tight and gas tight seal between the slideable plunger piston 57 and the inner surface 53 of the elonged hollow barrel 36.

The elonged hollow barrel 36 has a longitudinal axis 61 with a first end and a second end that extends from the first end of the elonged hollow barrel 36 to the second end of the elongated hollow barrel 36 or from the needle cannula 39 to the thumb flat 38.

Also shown inside of the elonged hollow barrel 36 is the slideable piston assembly 40. The slideable piston assembly 40 is comprised of the piston flange 49 and piston gasket 42 fixed at the second end of the slideable piston assembly 40 and the needle cannula 39 fixed at the first end of the slideable piston assembly 40.

The slideable piston assembly 40 is shown held in place by the barrel flange 62 near the first end of the piston assembly 40 and the piston gasket 42 at the second end of the piston assembly 40. The piston assembly 40 is further held in place by a compressed spring 41. The compressed spring 41 has a first end resting on the barrel flange 62 and a second end resting on the piston flange 49. The compressed spring 41 is pushing on the piston flange 49 of the slideable piston assembly 40. The slideable piston assembly 40 is held in place by the trigger 44 shown on each side of the elongated hollow barrel 36.

The syringe assembly 35 is shown held between finger 63 and finger 64 and it is further held and restrained from moving between finger 63 and finger 64 by the finger stops 65. The slideable plunger assembly 37 is depressed or pushed by pressure from the thumb 60 on the thumb flat 38. The slideable plunger assembly 37 is further pulled out of the elongated hollow barrel 36 of the syringe assembly 35 by pulling with the thumb 60 in the thumb ring 59.

Referring to FIG. 9 there is shown an enlarged partial section elevation of FIG. 8.

The slideable plunger assembly 37 has been moved from the second end of the elongated hollow barrel 36 to the first end of the elongated hollow barrel 36 causing the medicament to be injected into a patient. The spring 41 is shown compressed between the barrel flange 62 and the piston flange 49. The slidable piston assembly 40 and the needle cannula 39 are held firmly and rigidly in place in the elongated hollow barrel 36 by the combination of the barrel flange 62 supporting the first end of the slideable piston assembly 40 and the piston gasket 42 at the second end of the slideable piston assembly 40; this prevents movement of the slideable piston assembly 40 in a direction that is perpendicular to the longitudinal axis 61 of the elongated hollow barrel 36. The slideable piston assembly 40 and the needle cannula 39 are further held firmly and rigidly within the elongated hollow barrel 36 by the compressed spring 41 in combination with the one or two triggers 44 that restrain the spring 41 from thrusting the slidable piston assembly 40 and needle cannula 39 in a thumbward direction 51.

The trigger 44 is shown inserted into the piston notch 66 in the piston flange 49; the trigger 44 further extends through the trigger slot 67 in the barrel 36. The trigger 44 further is connected to the lever bar 48 by the trigger pin 56, which allow the lever bar 48 to rotate around the trigger 44. The fulcrum 47 is fixed to the barrel 36 at the first end of the fulcrum 47 and the fulcrum 47 is further connected to the lever bar 48 at the second end by the fulcrum pin 55. The lever bar 48 is connected to the trigger 44 at the first end of the lever bar 48 by the trigger pin 56 and the lever bar 48 is connected to the fulcrum 47 by the fulcrum pin 55 near the center of the lever bar 48. The lever bar 48 is further extended past the fulcrum 47 at the second end of the lever bar 48. The lever bar 48 is protected from being depressed by accident by the lever bar guard 68.

Figure 10:
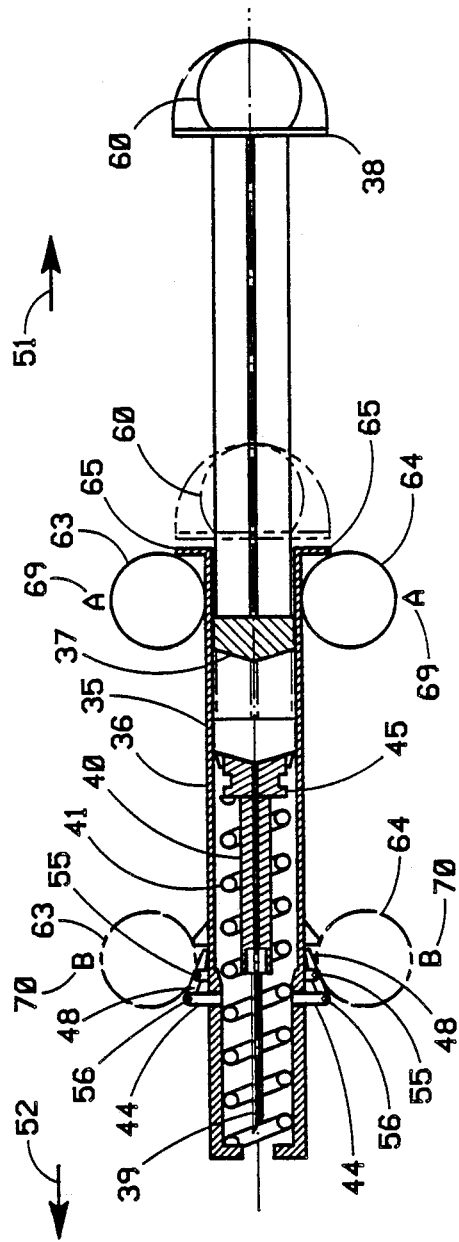
FIG. 10 is a section elevation view of the second preferred embodiment showing the piston assembly with the needle inside of the barrel.

Referring to FIG. 10 there is shown a section elevation view of the syringe assembly 35 of the second preferred embodiment after the trigger 44 has been withdrawn from the trigger notch 45 allowing the spring 41 to push the slideable piston assembly 40 and the needle cannula 39 into the barrel 36 thus preventing the needle cannula 39 from pricking anyone.

The slideable plunger assembly 37 has already been depressed to the determined position as shown in FIG. 9. The thumb 60 and the thumb flat 38 are shown in position A 69, and the finger 63 and finger 64 are also shown in position A 69 still gripping the finger stops 65. Finger 63 and finger 64 are moved in a needleward direction 52 where they contact the second end of the lever bar 48 where finger 63 and finger 64 touch the second end of the lever bar 48 in position B 70 and further depress the second end of the lever bar 48, thus causing the lever bar 48 to compress the fulcrum pin 55 and pull on the trigger pin 56 further pulling the trigger 44 out of the trigger notch 45. When the trigger 44 is pulled out of trigger notch 45, the slideable piston assembly 40 and the needle cannula 39 are no longer restrained and will be thrust into the elongated hollow barrel 36 by the spring 41. After the trigger 44 releases the slidable piston assembly 40, finger 63 and finger 64 are pulled back to position A 69. If the spring 41 is not sufficiently powerful to push the slideable piston assembly 40 and the slideable plunger assembly 37 together in a thumbward direction 51, the thumb 60 in the thumb ring 59 will pull on the slideable plunger assembly until the needle cannula 39 is completely covered in the elongated hollow barrel 36.

Figure 11:
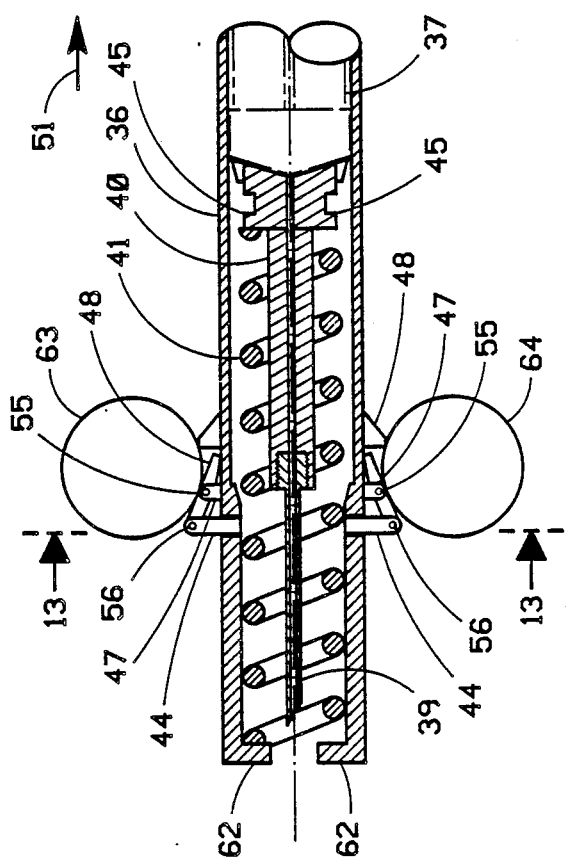
FIG. 11 is an enlarged section elevation view of a second preferred embodiment as taken from FIG. 10.

FIG. 11 is an enlarged section elevation of part of FIG 10 showing the slideable trigger 44 in greater detail.

The finger 63 and finger 64 are shown depressing the second end of the lever bar 48 thus pushing down on the fulcrum pin 55 and the fulcrum 47 and further pulling up on the trigger pin 56 and the trigger 44 which further pulls the trigger 44 from the trigger notch 45 which releases the slideable piston assembly 40. The slideable piston assembly 40 is shown being pushed in a thumbward direction 51 by the spring 41. As the slideable piston assembly 40 is being pushed in a thumbward direction 51 it will further carry the needle cannula 39 into the elongated hollow barrel 36 where the needle cannula 39 will be harmless and will be covered by the elongated hollow barrel 36 and the barrel flange 62. The slideable piston assembly 40 is also shown pushing the slideable plunger assembly 37 in a thumbward direction 51, however, if the spring 41 does not have sufficient strength, the thumb in the thumb ring will pull back on the plunger assembly only.

Figure 12:
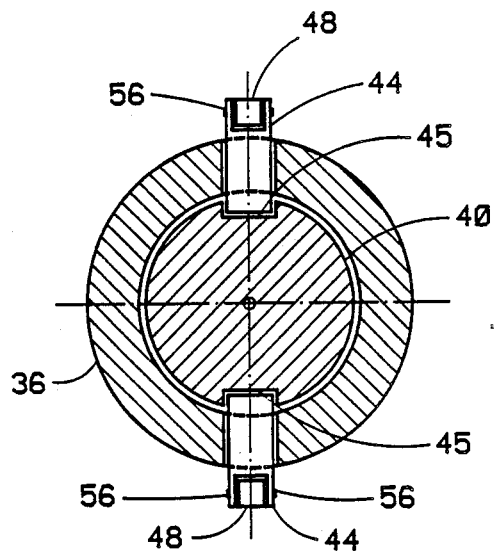
FIG. 12 is an enlarged section elevation as taken through FIG. 9.

Referring to FIG. 12 there is shown a section view as taken through FIG. 9.

The trigger 44 is shown inside of the trigger notch 45 that is in the slideable piston assembly 40. The trigger 44 is shown further extending through the elongated hollow barrel 36 where the trigger 44 is connected to the lever bar 48 by the trigger pin 56.

Figure 13:
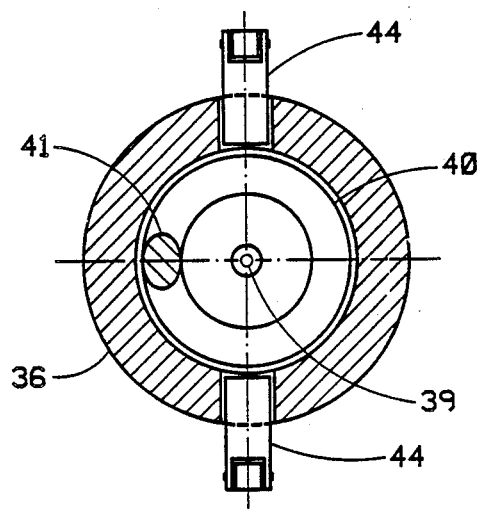
FIG. 13 is an enlarged section elevation as taken through FIG. 11.

Referring to FIG. 13 there is shown a section view as taken through FIG. 11.

The trigger 44 is withdrawn from the slideable piston assembly 40 and the spring 41 has pushed the slideable piston assembly 40 and the needle cannula 39 into the elongated hollow barrel 36.

Figure 14:
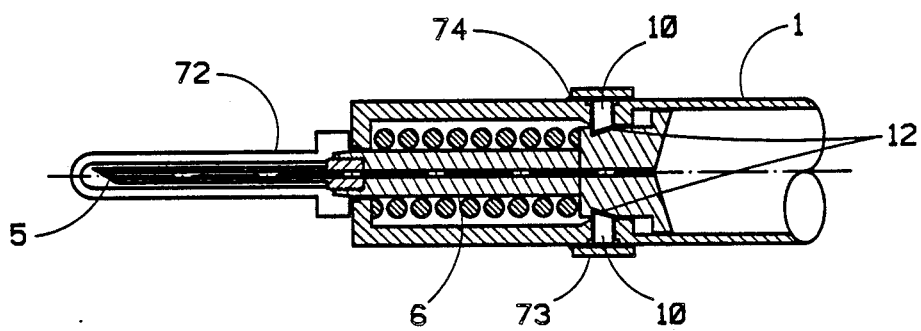
FIG. 14 is a section elevation of the first preferred embodiment showing the covers on the syringe needle and the trigger cover.

Referring to FIG. 14 there is shown a section elevation of the syringe assembly showing the means of protecting the syringe assembly 1 from being accidentally activated while being shipped or filled with medicament and further protecting the syringe assembly from other undesired contaminants.

The needle cannula 5 is shown covered with a needle protector 72 which is typical of any syringe used today. This needle protector 72 design is a matter of design choice. The slideable trigger 10 is shown protected by a trigger band 73 that is shown wrapped around the outside circumference of the syringe assembly 1 and held in place by a fillet of adhesive 74 or another suitable material. The trigger band 73 prevents the slideable trigger 10 from accidentally popping out of the trigger notch 12 in the slideable piston assembly 6.

Figure 15:
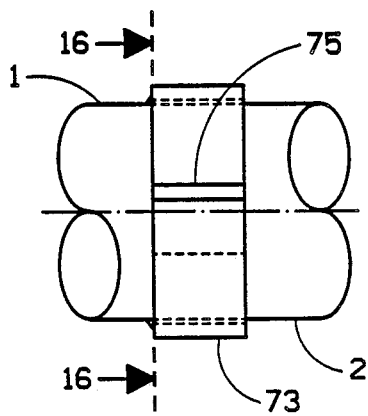
FIG. 15 is an elevation of the first preferred embodiment showing the trigger cover.

Referring to FIG. 15 there is shown an elevation of the trigger band 73 that is wrapped around the elongated hollow barrel 2 of the syringe assembly 1. The trigger band is shown with a tab 75 which will allow the user of the syringe assembly 1 to pull the trigger band 73 off of the syringe 1.

Figure 16:
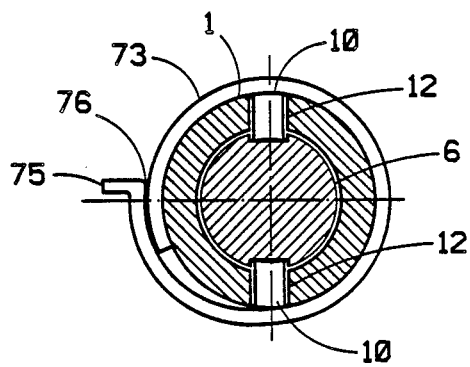
FIG 16 is a section elevation as taken through FIG. 15.

Referring to FIG. 16 there is shown section elevation as taken through FIG. 15.

The trigger band 73 is shown wrapped around the syringe assembly 1. The trigger band 73 is shown with a first end of the trigger band 73 being over lapped by the second end of the trigger band 73 and the second end of the trigger band 73 is fixed to the first end of the trigger band 73 with an adhesive 76 that can be broken by pulling on the tab 75 located at the second end of the trigger band 73.

As noted, the trigger band 73 is wrapped around syringe assembly 1 and it is shown holding the slideable trigger 10 inside of the trigger notch 12 in the piston assembly 6.

Figure 17:
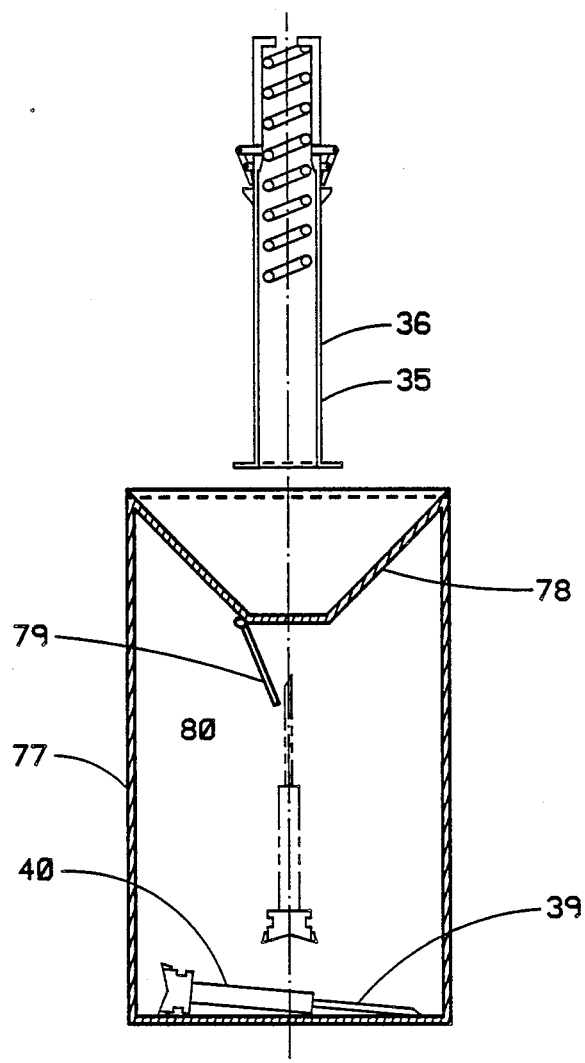
FIG. 17 is a section elevation of the second preferred embodiment showing the piston assembly with the needle being deposited into a container.

Referring to FIG. 17, there is shown a section elevation of the means of disposing of the used or contaminated needle cannula 39 of the second preferred embodiment. The needle cannula 39 is fixed to the slideable piston assembly 40 and the slideable plunger assembly is pulled out of the elongated hollow barrel 36 of the syringe assembly 35. The syringe assembly 35 is turned over to a position where the barrel 36 is over the container 77 and the needle 39 with the slideable piston assembly 40 falls out of the elongated hollow barrel 36 and into the container 77. The container 77 has four sides, a bottom and a top. The top of the container is a funnel 78 that will guide the needle cannula 39 and the slideable piston assembly 40 into the container 77 and will not allow anything to fall out if the container 77 is accidentally turned over. The container 77 can be equipped with a trap door 79 that will open with the weight of the needle cannula 39 and the slideable piston assembly 40 but will close by the spring means 80 at one end of the trap door 79 after the slideable piston assembly 40 and the needle cannula 39 have fallen into the container 77.

Figure 18:
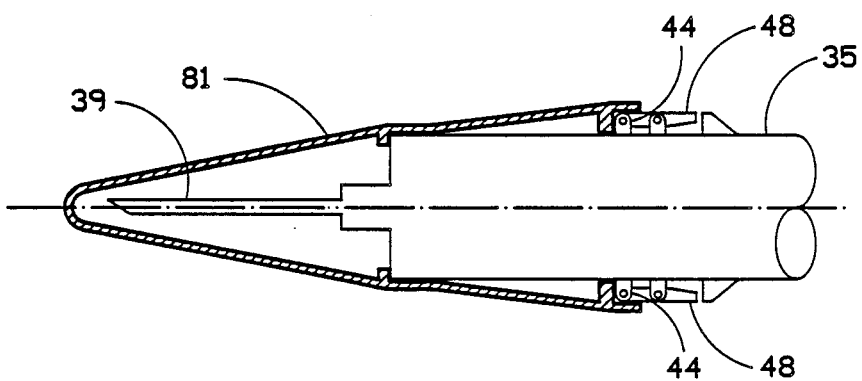
FIG. 18 is a section elevation showing a protective cover for the needle and the trigger device.

Referring to FIG. 18 there is shown a cover 81 over the syringe assembly 35 of the second preferred embodiment.

The cover 81 is shown covering the needle cannula 39 and the first end of the syringe assembly 35. The cover 81 also extends over the trigger 44 and part of the lever bar 48 to prevent the trigger 44 from being moved.

Although the system described in detail supra has been found to be most satisfactory and preferred many variations are possible. For example the syringe may have three or four triggers, the syringe could be square in section or the trigger could be placed closer to the needle.

Although the invention has been described with reference to the preferred embodiment, it will be understood by those skilled in the art, that additions, modifications, substitutions, deletions and other changes not specifically described, may be made in the embodiments herein, it should be understood that the details herein are to be interpreted as illustrative and are not in a limiting sense.

What is claimed as invention is:

1. A syringe assembly held by fingers and thumb for injecting medicament or fluid into a body or part of a body comprising:

a elongated hollow barrel having a first end and a second end, and having an inner surface and an outer surface and further having a longitudinal axis in the center of the said elongated hollow barrel parallel in most part to the said outer surface of the said elongated hollow barrel further extending from said first end to said second end;

a slideable plunger assembly inside of said elongated hollow barrel, said slideable plunger assembly having a first end and a second end and further having a plunger piston at said first end and a thumb flat at second end wherein a thumb or finger pushes on said thumb flat in a direction toward said first end;

a slideable piston assembly inside of said elongated hollow barrel, said piston assembly having a first end and a second end and said first end of said piston assembly is nearer said first end of said elongated hollow barrel;

a needle cannula having a first end and a second end, said first end of said needle cannula extends past said first end of said elongated hollow barrel and said second end of said needle cannula is fixed to said first end of said slideable piston assembly.

a spring means having a first end and a second end, said first end of said spring means is integral with said first end of said elongated hollow barrel and said second end of said spring means is integral with said slideable piston assembly, said spring means is further compressed between said first end of said elongated hollow barrel and said slideable piston assembly;

at least one trigger notch formed into said slideable piston assembly, said trigger notch further having at least, a first side and a second side, said first side is near perpendicular to said longitudinal axis of said elongated hollow barrel and said first side is nearer to said first end of said slideable piston assembly and said second side of said trigger notch is a trigger notch slope wherein said trigger notch slope is near to said first side of said trigger notch and slopes away from said first side in the direction of said second end of said slideable piston assembly;

at least one trigger guide formed in the said elongated hollow barrel and extending from said outer surface of said elongated hollow barrel to said inner surface of said elongated hollow barrel.

at least one slideable trigger, having a first end and a second end, said slideable trigger is held in place within said trigger guide wherein said first end of said slideable trigger is located near the outer surface of said elongated hollow barrel and said slideable trigger further extends past said trigger guide and engages said trigger notch formed into said slideable piston, said second end of said slideable trigger having a slope similar to said trigger slope and wherein the said first end of the said slideable plunger assembly is pushed by said finger or thumb into the second end of the said slideable piston assembly further pushing said slideable piston assembly toward the first end of said elongated hollow barrel thereby further compressing the said spring means and further causing the said trigger notch slope to further push on the slope of the said slideable trigger, further causing the said slideable trigger to slide in a direction away from the said longitudinal axis of the said elongated hollow barrel and wherein said sliding trigger no longer engages the said trigger notch and wherein said finger or thumb is further removed from the said thumb flat thus allowing the said spring means to push on the slideable piston assembly which will also push on the slideable plunger assembly thus forcing the needle cannula to move into the first end of said elongated hollow barrel wherein said needle cannula will be completely enclosed by said elongated hollow barrel wherein said needle cannula cannot accidentally prick or injure anyone.

2. The syringe assembly of claim 1 wherein said elongated hollow barrel further has a flange at said first end of said elongated hollow barrel and said flange further has a barrel flange gasket fixed to said flange and said barrel flange gasket further forms a fluid tight seal between said flange and said slideable piston assembly.

3. The syringe assembly of claim 1 including a gasket means on said slideable piston assembly wherein said gasket means forms a fluid tight seal between said slideable piston assembly and said inner surface of said elongated hollow barrel.

4. The syringe assembly of claim 1 wherein said slideable trigger further includes a trigger gasket or seal around said trigger means and said trigger guide to form a fluid tight seal to further prevent contamination from entering into said syringe assembly;

said trigger gasket to further prevent said slideable trigger from falling out of said syringe assembly.

5. The syringe assembly of claim 1 wherein said spring means is only partially compressed while said syringe assembly is being used to inject medicament into a body or part of a body.

6. The syringe assembly of claim 1 wherein said syringe assembly may also be used to draw fluid out of a body or part of a body.

7. A syringe assembly that is held by fingers and thumb for injecting medicament or fluid into a body of part of a body comprising:

an elongated hollow barrel having a first end and a second end and having an inner surface and an outer surface and further having a longitudinal axis in the center of the said elongated hollow barrel, parallel in most part to the said inner surface and the said outer surface of the said elongated hollow barrel and further extending from said first end to said second end of said elongated hollow barrel;

a slideable plunger assembly inside of said elongated hollow barrel, said slideable plunger having a first end and a second end and further having a plunger piston at said first end and a thumb flat and a thumb ring at said second end and wherein a thumb or finger pushes on said thumb flat in a direction toward said first end and a thumb or finger pulls on the thumb ring in a direction toward said second end;

a slideable piston assembly inside of said elongated hollow barrel, said piston assembly having a first end and a second end and said first end of said piston assembly is near said first end of said elongated hollow barrel;

a needle cannula having a first end and a second end, said first end of said needle cannula extends past said first end of said elongated hollow barrel and said second end of said needle cannula is fixed to said first end of said slideable piston assembly;

a spring means having a first end and a second end, said first end of said spring is integral with said first end of said elongated hollow barrel and said second end of said spring means is integral with said slideable position assembly, said spring means is further compressed between said first end of said elongated hollow barrel and said slideable piston assembly;

at least one trigger notch formed into said slideable position assembly, said trigger notch further having at least two sides, with each side being near perpendicular to the said longitudinal axis of the elongated hollow barrel;

at least one trigger slot formed in the said elongated hollow barrel and extending from said outer surface of said elongated hollow barrel to said inner surface of said elongated hollow barrel;

at least one slideable trigger having a first end and a second end, said slideable trigger extends through said trigger slot and said slideable trigger is further inserted into said trigger notch formed in said slideable piston assembly, said second end of said slideable trigger is similar in shape to said trigger notch;

a lever bar said lever bar having a first end and a second end and said lever bar is flexibly fixed to said slideable trigger at said first end of said of said lever bar by a trigger pen;

a fulcrum means with a first end and a second end, said fulcrum means is fixed to said elongated hollow barrel at said first end of said fulcrum means and second end of said fulcrum means is further flexibly fixed to said lever bar between said first end of said lever bar and said second end of said lever bar by a fulcrum pin and wherein said syringe assembly is used to inject medicament or fluid into a said body or said part of a body and after said needle cannula has entered into said body or said part of said body, at least one lever bar is depressed at said second end of said lever bar which causes said lever bar to pull on said slideable trigger further pulling said first end of said slideable trigger out of said trigger notch thus further releasing said slideable piston assembly from said slideable trigger which further allows said spring means to thrust said slideable piston assembly and said needle cannula into said elongated hollow barrel wherein said elongated hollow barrel completely encloses said needle cannula wherein said needle cannula cannot accidentally prick or injure a person.

8. The syringe assembly of claim 7 wherein said elongated hollow barrel further includes a barrel flange fixed on said first end of said elongated hollow barrel.

9. The syringe assembly of claim 7 including a gasket means on said slideable piston assembly wherein said gasket means forms a fluid tight seal between said slideable piston assembly and said inner surface of said elongated hollow tube.

10. The syringe assembly of claim 7 wherein the thumb is inserted into said thumb ring and further pulls back on said thumb ring and further pulls said slideable plunger assembly partially out of said elongated hollow tube.

11. The syringe assembly of claim 7 including a lever bar guard, said lever bar guard to protect said lever bar from being depressed accidentally.

12. A syringe assembly comprising:
an elongated hollow barrel;
a slideable position assembly;
a needle cannula;
at least one trigger means;
a trigger band; said trigger band having a width greater than the width of said trigger means and said trigger band having a first end and a second end and said trigger band is further wrapped completely around the circumference of said elongated hollow barrel until said second end of said trigger band overlaps said first end of said trigger band; adhesive means, wherein said adhesive means is placed between said first end of said trigger band and said second end of said trigger band further fixing said first end of said trigger band to said second end of said trigger band;
a tab fixed to said second end of said trigger band and projecting from said trigger band wherein said trigger band will prevent said trigger means from falling out of said slideable piston assembly and elongated hollow barrel prior to the syringe assembly being used and wherein said tab is pulled, thus pulling said second end of said trigger band off of said first end of said trigger band and further pulling off said trigger band from said elongated hollow barrel, thus making said syringe ready for use.

13. The syringe assembly of claim 12 including a needle cannula protector, said needle cannula -protector to fit over said needle cannula and to be further held in place by friction and wherein said needle protector will be removed prior to the use of said syringe assembly.

14. The syringe assembly of claim 12 including adhesive fixing said trigger band to said elongated hollow barrel.

15. The assembly of claim 7 further including a container assembly for disposal of part of said syringe assembly or all of said syringe assembly comprising;,
four sides and a bottom to form a box;
a funnel forming the top of said container;
a trap door at the narrowmost end of said funnel;
a hinge fixed to said trap door and further fixed to said funnel;
a spring further fixed to said trap door and said funnel wherein said slideable plunger assembly is remove from said syringe assembly and said elongated hollow barrel is turned over said container assembly, allowing said slideable piston assembly with said needle cannula to fall into said funnel of said container assembly, said slideable piston assembly and said needle cannula will further fall through said trap door and into said container assembly wherein said trap door will close by means of said spring fixed to said trap door, wherein said slideable position assembly and needle cannula cannot fall out of said container assembly.

16. The container assembly of claim 15, wherein said container assembly will be destroyed while containing said slideable piston assembly and said needle cannula.

* * * * *